United States Patent [19]

Heimbürger et al.

[11] Patent Number: 4,579,735
[45] Date of Patent: Apr. 1, 1986

[54] PROCESS FOR THE PASTEURIZATION OF HUMAN RESIDUAL PLASMA

[75] Inventors: Norbert Heimbürger; Hermann E. Karges, both of Marburg; Gerhardt Kumpe, Wetter; Wilfried Wormsbächer, Kirchhain, all of Fed. Rep. of Germany

[73] Assignee: Behringwerke Aktiengesellschaft, Marburg/Lahn, Fed. Rep. of Germany

[21] Appl. No.: 643,720

[22] Filed: Aug. 24, 1984

[30] Foreign Application Priority Data

Aug. 26, 1983 [DE] Fed. Rep. of Germany ....... 3330770

[51] Int. Cl.$^4$ ............................................. A61K 35/16
[52] U.S. Cl. .................................................... 424/101
[58] Field of Search ......................................... 424/101

[56] References Cited

U.S. PATENT DOCUMENTS 4,327,086 4/1982 Fukushima et al. ................ 424/101
4,446,134 5/1984 Naito et al. ......................... 424/101

Primary Examiner—Sam Rosen
Attorney, Agent, or Firm—Finnegan, Henderson, Farabow, Garrett & Dunner

[57] ABSTRACT

A process for the preparation of a pasteurized human citrated plasma is described, in which citrated plasma, from which the prothrombin factors and labile proteins have been removed, is heated in the presence of stabilizers.

8 Claims, No Drawings

PROCESS FOR THE PASTEURIZATION OF HUMAN RESIDUAL PLASMA

The invention relates to a process for the preparation of a pasteurized human citrated plasma and to a product prepared by this process.

Large amounts of fresh plasma and fresh-frozen plasma (FFP) are used in clinical routines. The main indications are topping up of the blood volume to maintain the oncotic pressure, blood loss following major operations and accidents and treatment of various forms of shock and first dressing of polytraumatized patients. Only a plasma which, where possible, contains all the proteins in natural form, in particular the enzymes and inhibitors of the coagulation system, the kallikrein-kinine system and the complement reaction, as well as the transportation proteins and antibodies is indicated for the care of these patients.

The risk of transfer of hepatitis is a general problem in the use of fresh plasma and also FFP. This risk is lower if the blood donors are monitored, but this can be ensured in only a few cases.

The risk of hepatitis results from two causes: firstly, the test systems for hepatitis B virus are not sufficiently sensitive unambiguously to exclude a risk of infection; secondly, there is as yet still no test for the non-A/non-B hepatitis. Finally, there is also the risk of transfer of other viruses, such as, for example, Epstein Barr and cytomegaly, that is to say, the use of stored blood would in each case require a large number of relatively expensive investigations, apart from the fact that there are still no methods available for identification and quantification of certain viruses.

This state of development shows that there is an urgent need for a process which allows pasteurization of plasma whilst retaining the naturalness of the individual plasma proteins with their different biochemical functions.

Viruses are killed by pasteurization, as has already been shown in the example of albumin. Such processes for the pasteurization of blood constituents are known for certain coagulation factors, besides albumin. German Offenlegungsschrift No. 2,916,711 describes a process which enables solutions of coagulation factors II, VIII and XIII and of antithrombin III and plasminogen to be pasteurized, amino acids and saccharides or sugar-alcohols being added. In this manner, heating to 60° C. for 10 hours is possible, this virtually excluding the risk of transfer of hepatitis.

The invention was thus based on the object of providing a process for the pasteurization of human plasma which can be applied to a natural plasma, causes no great losses in activity of the plasma proteins and ensures that a hepatitis-safe product results.

A precondition for achieving the object was that the plasma is heated, for example, at 60° C. for 10 hours. However, it is known that the fibrinogen and also other plasma proteins are denatured and precipitate only a few minutes after being warmed to 60° C.

It was therefore surprising that it was possible, with the aid of certain additives, such as carbohydrates and amino acids and divalent metal ions, to stabilize the plasma such that it was possible to heat it at 60° C. for 10 hours without substantial losses in protein and activity, when the prothrombin factors (factor II, VII, IX and X) had first been removed from deep-frozen and rethawed human citrated plasma, for example by adsorption on $Al(OH)_3$, $Ca_3(PO_4)_2$ or DEAE-Sephadex and the labile proteins, in particular lipoproteins, had been removed by adsorption on polyhydroxymethylene in accordance with the German Patent Application of Behringwerke AG 83/B 014 or on a silica gel, for example Aerosil, or by flotation of the lipoproteins with organic solvents, contamination by hepatitis B viruses also being reduced.

The invention thus relates to a process for the pasteurization of a human "residual" plasma, which comprises removing the prothrombin factors and labile proteins from human citrated plasma, and heating the residual plasma in the presence of an amino acid and a carbohydrate and, if appropriate, ions of a divalent metal.

For safety reasons, a starting material in which no hepatitis viruses can be detected by a known test, for example a radioimmunoassay (RIA) is as far as possible used, although the process claimed can also be applied to starting materials which do not fulfill this criterion. On the other hand, a negative test result does not guarantee freedom from the virus, as already described. A carbohydrate and an amino acid, as well as divalent metal ions, preferably calcium or magnesium ions, are added for stabilization of the plasma proteins for the pasteurization, and the mixture is heated.

One of the amino acids glycine, $\alpha$- or $\beta$-alanine, hydroxyproline, proline, glutamine and $\alpha$-, $\beta$- or $\gamma$-aminobutyric acid, but preferably glycine, and a mono- or oligo-saccharide or a sugar-alcohol, preferably sucrose, are particularly suitable for the stabilization.

The amino acid is added in an amount of 0.25 to 3 moles/liter, preferably 1 mole/liter, and 35 to 100 g, preferably 100 g, of carbohydrate are mixed with 100 ml of the plasma protein solution; in the preferred procedure, the solution formed then contains the carbohydrate in a concentration of 60 g/100 ml.

Divalent metal ions are added in an amount of 1 to 100 mmoles, preferably 15 mmoles, per liter of solution.

The mixture is heated at a temperature between 30° C. and 100° C., preferably at 50° C. to 70°, for 1 minute to 48 hours, preferably for 5–15 hours, the highest temperature being allocated the shortest time and vice versa.

Thereafter, the stabilizers can be removed. Equilibrium dialysis, concentration on an ultrafilter, sterile filtration and/or bottling can then follow.

As will be shown in the following examples, it was possible, by the process described, to pasteurize plasma whilst retaining the biological activity of the most important proteins, including the coagulation factors and their inhibitors. Moreover, it has been found that the antibody action of the immunoglobulin is also retained after the pasteurization. No indication that fragmentation of proteins occurs during the heating has been obtained by the analysis methods customary in protein chemistry.

A particularly suitable process for the preparation of a hepatitis-safe, natural human plasma product is the following: adsorption of the prothrombin factors on $Al(OH)_3$, filtration of the adsorbed plasma over a column of polyhydroxymethylene (PHM) and stabilization of the column eluate by addition of 100 g of sucrose per 100 ml of eluate and 1 mole of glycine and 15 mmoles of calcium ions per liter of solution. The prothrombin factors removed before the heating can be eluted from the $Al(OH)_3$ and, having been separately pasteurized, then added to the plasma again.

EXAMPLE 1

Starting material: 500 ml of deep-frozen human citrated plasma. The plasma was thawed at 20° C. and stirred twice with 25 ml of 1% strength Al(OH)$_3$ suspension for 15 minutes to remove the prothrombin factors and then centrifuged. The Al(OH)$_3$ residue was discarded.

Stabilization and pasteurization: 7.5 ml of a CaCl$_2$ solution containing 1 mole/liter were pipetted into 500 ml of the adsorbed plasma so that the final Ca$^{2+}$ concentration was 15 mmoles/liter; 500 g of sucrose were then added, with further stirring and warming, and, after this had dissolved completely, 37.5 g of glycine (1 mole/liter) were added. The pH value was then brought to 7.3 with 2N NaOH and adjusted until constant.

The volume increased from 500 ml to 850 ml of a clear viscous solution, as a result of the additives, and the solution was heated at 60° C. in a water bath for 10 hours. The solution was also clear after the heating.

Removal of the stabilizers: After the pasteurized solution had been cooled, it was diluted with a citrate/NaCl buffer (0.01 mole/liter of tri-Na-citrate, pH 7.5; 0.06 mole/liter of NaCl) to 2500 ml, dialyzed on an ultra-filter against 5 liters of a buffer of the same composition and concentrated to 500 ml. After the plasma starting volume had been reached (500 ml), the mixture was diluted again to 2500 ml and dialyzed again against 5 liters of fresh buffer. After the dialysis equilibrium had been reached, and the mixture had been concentrated to 500 ml, the filtration was interrupted. A solution slightly clouded by lipoproteins was obtained as the end product.

The pasteurized plasma was ultracentrifuged at 20° C. and 30,000 g for 1 hour and was clarified by filtration and subsequently sterilized by filtration over Seitz membrane filters, bottled in 100 ml infusion bottles containing 50 ml and lyophilized. Table 1 contains the protein and function determinations of the biologically most important proteins before and after pasteurization, lyophilization and reconstitution in water for injection purposes.

EXAMPLE 2

Starting material: 6 g of suction filter-moist DEAE-Sephadex A-50 equilibrated in citrate/NaCl buffer (0.02 mole/liter of tri-Na citrate solution, pH 7.5; 0.06 mole/liter of NaCl) were added to 500 ml of pooled fresh human citrated plasma at 20° C. for removal of the prothrombin factors, the mixture was stirred for 30 minutes and the DEAE-Sephadex was removed by centrifugation. For adsorption of the lipoproteins and hepatitis B viruses, the supernatant liquor was passed over a column with 500 ml of polyhydroxymethylene, which had been equilibrated with a solution containing 0.01 mole/liter of tri-Na citrate, pH 7.5, and 0.06 mole/liter of NaCl. After passage through the column, 550 ml of clear, lipoprotein-free plasma were obtained.

Stabilization and pasteurization: 8.25 ml of a CaCl$_2$ solution containing 1 mole/liter were added to 550 ml of delipidized human plasma, and 550 g of sucrose were then added, with stirring and warming to 30° C. After the sucrose had dissolved, 41.5 g (1 mole/liter) of glycine were stirred into the solution. The pH value was brought to 7.3 with 2N NaOH and was regulated until constant.

The clear viscous solution (930 ml) thus stabilized was kept at 60° C. in a water bath for 10 hours. The solution was also clear after heating.

Removal of the stabilizers: The cooled solution was diluted with a citrate-NaCl buffer (0.01 mole/liter) of tri-Na citrate, pH 7.5; 0.06 mole/liter of NaCl) to 2750 ml and dialyzed on an ultrafilter against 5 liters of a buffer of the same composition and concentrated to 500 ml. It was diluted again and dialyzed against fresh buffer. After the dialysis equilibrium had been reached and the end volume was 500 ml, a clear solution resulted, which was clarified and sterilized by filtration over Seitz membrane filters, bottled in 100 ml infusion bottles containing 50 ml and lyophilized.

Table 1 contains the concentration and activity of selected plasma proteins before and after pasteurization. The antibody activities before and after heating are summarized in Table 2.

TABLE 1

Total protein, fibrinogen and fibronectin content and activities of selected coagulation factors and inhibitors before and after pasteurization of human plasma

| Treatment of the plasma | Protein mg/ml | Fibrinogen mg/dl | Fibronectin mg/dl | F V % of the norm* | F VIII % of the norm | F XI % of the norm | F XII % of the norm | HMW kininogen % of the norm | AP % of the norm | AT III % of the norm | Apo A mg/dl | Apo B mg/dl |
|---|---|---|---|---|---|---|---|---|---|---|---|---|
| Untreated (before pasteurization) | 44 | 212 | 25 | 60 | 70 | 100 | 100 | 90 | 93 | 92 | 134 | 79 |
| After pasteurization according to Example 1 | 39 | 169 | 19.3 | 13 | 34 | 21 | 60 | 55 | 82 | 77 | 98 | 81 |
| After pasteurization according to Example 2 | 35 | 224 | 19.3 | 5 | 27 | 36 | 50 | 36 | 67 | 83 | 4 | 10 |

*"Norm" = content of a plasma pool from at least 40 healthy male donors (= 100%)
AT III = Antithrombin III
AP = $\alpha_2$Antiplasmin
HMW = High Molecular Weight kininogen
Apo = Apolipoprotein A and B.

TABLE 2

Antibody titer in the plasma before and after pasteurization according to Example 2

| Plasma | Rubella | Morbilli | Tetanus (IU/ml) |
|---|---|---|---|
| Before pasteurization | 1:150 | 1:64 | 1 |
| After pasteurization | 1:120 | 1:64 | 1 |

We claim:

1. A process for the pasteurization of a human residual plasma, which comprises removing the prothrombin factors and labile proteins from human citrated plasma to form the human residual plasma, and heating the residual plasma in the presence of (1) an amino acid, (2) a carbohydrate and (3) a divalent metal ion.

2. The process as claimed in claim 1, wherein the prothrombin factors and labile proteins are removed by means of a polyhydroxymethylene which contains a grafted oxyethylated alcohol or a grafted oxyethylated carboxylic acid.

3. The process as claimed in claim 1, wherein the amino acid is glycine, $\alpha$- or $\beta$-alanine, hydroxyproline, proline, glutamine or $\alpha$-, $\beta$-or $\gamma$-aminobutyric acid in a concentration of 0.25–3 moles/liter.

4. The process as claimed in claim 1, wherein the carbohydrate is sucrose in a concentration of 35–60 g/100 ml of solution.

5. The process as claimed in claim 1, wherein the divalent metal ions are Ca ions in a concentration of 1–100 mmoles/liter.

6. The process as claimed in claim 1 wherein heating is carried out at a temperature of 50°–70° C. for 5–15 hours.

7. A plasma product prepared by the process as claimed in claim 1.

8. The process of claim 1 wherein said carbohydrate is selected from the group consisting of monosaccharides, oligosaccharides and sugar alcohols.

* * * * *